United States Patent [19]

Robert

[11] Patent Number: 5,296,069

[45] Date of Patent: Mar. 22, 1994

[54] PROCESS FOR MANUFACTURING IMPLANTS HAVING COATED SURFACES

[75] Inventor: Antoine J. H. Robert, Rio de Janeiro, Brazil

[73] Assignee: Silimed-Silicone E. Instrumental Medico Cirurgico E. Hosiptalar Ltda., Rio de Janeiro, Brazil

[21] Appl. No.: 923,230

[22] Filed: Jul. 31, 1992

[30] Foreign Application Priority Data

Dec. 27, 1991 [BR] Brazil .................... PI 9105626

[51] Int. Cl.⁵ .................. B29C 35/02; B32B 31/06
[52] U.S. Cl. ...................... 156/242; 156/245; 623/8; 623/11
[58] Field of Search .............. 156/242, 245; 623/8, 623/11

[56] References Cited

U.S. PATENT DOCUMENTS

| | | | |
|---|---|---|---|
| 3,366,975 | 2/1968 | Pangman | 623/8 |
| 3,559,214 | 2/1971 | Pangman | 623/8 |
| 3,683,424 | 8/1972 | Pangman | 623/8 |
| 3,879,245 | 4/1975 | Fetherston et al. | 156/245 |
| 4,205,401 | 6/1980 | Frisch | 623/8 |
| 5,141,581 | 8/1992 | Markham | 156/242 |

*Primary Examiner*—Caleb Weston
*Attorney, Agent, or Firm*—Curtis, Morris & Safford

[57] ABSTRACT

A process for manufacturing surgical implants is provided with a surgical coating, which neither comes loose upon surgical handling nor causes user discomfort, lesion or infection. The process comprises the steps of disposing a silicone sheet over a foam sheet, and exerting pressure to adhere the same. The assembly thus formed is placed on a mounting base which will receive the implant with another silicone/foam sheet assembly being disposed over the same. The implant is then placed in a mold which will exert a uniform pressure on the implant to adhere the two silicone sheets and foam sheet assemblies to the implant.

4 Claims, No Drawings

PROCESS FOR MANUFACTURING IMPLANTS HAVING COATED SURFACES

The present invention relates to a process for manufacturing coated implants adequate for surgical implants in cases where an increase, correction or reconstitution of users' body parts, such as, for example, mammary prostheses, are required. Such prosthesis may have any size or shape.

The prosthesis or implant here mentioned consists preferably of a silicone bag or envelope already filled to a desired volume with a material which may be, for example, silicone gel or saline solution. Of course, any other material might be employed, provided it is an amorphous and nonreactive material.

Implants coated with a foamlike material are currently used, which have had several drawbacks both during and after surgery since foam detachs itself from the implant upon handling releasing pieces, and a connective tissue capsule may also form upon contact with the foam favoring infections.

An object of the present invention is to provide a prosthesis whose surfaces are coated with an amorphous material which does not come loose.

Another object is to provide an implant having an improved surface so that contact with the user's tissues does not cause discomfort, lesions or infections, additionally not requiring a larger surgical incision since its thickness is extremely small.

The objects of the present invention are achieved by providing a process for manufacturing implants having coated surfaces, said implant initially having smooth surfaces already filled with silicone gel or another appropriate material.

According to the present invention, said implant consists basically of a baglike envelope of a material such as silicone, which is filled with saline solution or silicone gel, taking thus an appropriate shape for the desired use.

A nonvulcanized silicone sheet is disposed over a sheet of polyurethane or silicone foam or any other appropriate material.

The assembly consisting of a silicone sheet and a foam sheet will be subjected to the pressure exerted by means of two parallel and spaced apart rollers so as to adhere said assembly by means of pressure.

The assembly thus formed is placed on a auxiliary mounting base. Said base will then receive a ready implant, that is, having smooth surfaces and already filled with gel or saline solution, part of said assembly having a silicone sheet facing said implant. Thereafter, said implant is centered and a pressure is exerted over the same so as to establish an adhering position for said implant and assembly.

Another silicone sheet and foam sheet assembly is placed over another face of said implant such as above described. Also, the silicone sheet must be facing said implant.

The auxiliary mounting base is fitted in a mold, by means of which a uniform pressure is exerted throughout the whole implant surface in order to adhere said silicone sheet and foam sheet assemblies to said implant.

By means of an appropriate tool pressure is exerted on said mold periphery in order to achieve a maximum adherence region between said two silicone sheet and foam sheet assemblies.

Thereafter, the already coated implant is removed from said mold, the coating vulcanization being then processed making said implant ready to use.

Said coated implant, such as described in the present invention, must undergo mechanical resistance testing and a test to verify the coating over the implant adherence.

It must be understood that small variations are possible provided they do not deviate from the scope of attached claims.

I claim:

1. Process for manufacturing implants having coated surfaces, said implant being already filled with gel and having smooth surfaces, comprising the steps of:
   a) disposing a nonvulcanized silicone sheet over a foam sheet to form a silicone sheet and foam sheet assembly;
   b) passing the silicone sheet and foam sheet assembly through two parallel and spaced apart rollers so as to exert a predetermined pressure for adhering said assembly;
   c) attaching said silicone sheet and foam sheet assembly to an auxiliary mounting base;
   d) placing the smooth and filled implant in contact with one face of the silicone sheet;
   e) centering said implant and exerting pressure on the same in order to establish an adhering position;
   f) placing upon another face of the implant another silicone sheet and foam sheet assembly such that the silicone sheet contacts said implant to form an implant assembly;
   g) disposing said implant assembly in a mold for uniform mechanical pressure throughout the entire surface of the implant assembly;
   h) pressing the periphery of the mold in order to achieve a maximum adherence region between said two silicone and foam sheet assemblies; and
   i) removing said implant from said mold.

2. The process according to claim 1, wherein the coated implant is vulcanized just after step (i).

3. The process according to claim 2, wherein after vulcanization a mechanical resistance test for the implant is effected.

4. The process according to claim 2, wherein after said vulcanization a coating adherence test is effected for said implant.

* * * * *

UNITED STATES PATENT AND TRADEMARK OFFICE
CERTIFICATE OF CORRECTION

PATENT NO. : 5,296,069
DATED : March 22, 1994
INVENTOR(S) : Antoine Jean Henri Robert It is certified that error appears in the above-identified patent and that said Letters Patent is hereby corrected as shown below:

ON THE COVER PAGE, ITEM [73] ASSIGNEE:

The Assignee "Silimed-Silicone E. Instrumental Medico Cirurgico E. Hosiptalar Ltda." should be changed to —Silimed-Silicone e Instrumental Medico Cirurgico e Hospitalar Ltda.—

Signed and Sealed this

Twentieth Day of September, 1994

Attest:

BRUCE LEHMAN

Attesting Officer

Commissioner of Patents and Trademarks